United States Patent [19]

Bodor et al.

[11] 4,189,571
[45] Feb. 19, 1980

[54] ESTERS OF CROMOGLYCATES

[75] Inventors: Nicholas S. Bodor; Jack A. Zupan, both of Lawrence, Kans.

[73] Assignee: Fisons Limited, London, England

[21] Appl. No.: 875,902

[22] Filed: Feb. 7, 1978

[51] Int. Cl.² .................. C07D 311/22; A61K 31/35
[52] U.S. Cl. ................................. 542/427; 260/345.2; 424/283
[58] Field of Search ................. 260/345.2, 345.5; 542/413, 426, 427

[56] References Cited

U.S. PATENT DOCUMENTS

| | | | |
|---|---|---|---|
| 3,686,320 | 8/1972 | Fitzmaurice et al. | 260/345.2 |
| 3,790,580 | 2/1974 | Bennett et al. | 260/345.2 |

*Primary Examiner*—Nicky Chan
*Attorney, Agent, or Firm*—Merriam, Marshall & Bicknell

[57] ABSTRACT

There are described compounds of formula I,

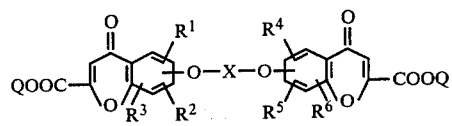

in which
$R^1$, $R^2$, $R^3$, $R^4$, $R^5$ and $R^6$ are the same or different and each represent hydrogen, halogen, hydroxy, alkyl C 1 to 6, alkoxy C 1 to 6, hydroxy-alkoxy C 1 to 6, or alkoxy C 1 to 6-alkoxy C 1 to 6, X is a straight or branched C 2 to 10 hydrocarbon chain which may be substituted by an —OH group, Q is a group —CHR—Z R is hydrogen, alkyl C 1 to 8, phenyl, or alkoxy (C 1 to 8)-carbonyl, Z is a group —O—CO—Ra, —CO—ORa or —CONRbRc, Ra is cyclohexyl or cyclopentyl; straight or branched alkyl C 1 to 12, which is optionally substituted by cyclohexyl or cyclopentyl; alkenyl C 2 to 6, which is optionally substituted by phenyl; or, when Z is —CO—ORa, hydrogen, and Rb and Rc, which are the same or different, are each alkyl C 1 to 12.

There are also described processes for making the compounds, and pharmaceutical, e.g. anti-allergic, compositions containing the compounds.

11 Claims, No Drawings

ESTERS OF CROMOGLYCATES

The present invention relates to new chemical compounds, methods for their preparation and pharmaceutical compositions containing them.

According to our invention we provide compounds of formula I,

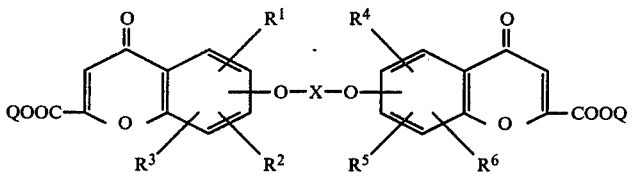

in which
R¹, R², R³, R⁴, R⁵ and R⁶ are the same or different and each represent hydrogen, halogen, hydroxy, alkyl C 1 to 6, alkoxy C 1 to 6, hydroxy-alkoxy C 1 to 6, or alkoxy C 1 to 6-alkoxy C 1 to 6, X is a straight or branched C 2 to 10 hydrocarbon chain which may be substituted by an —OH group, Q is a group —CHR-Z, R is hydrogen, alkyl C 1 to 8, phenyl, or alkoxy (C 1 to 8)-carbonyl, Z is a group —O—CO—Ra, —CO—ORa or —CONRbRc, Ra is cyclohexyl or cyclopentyl; straight or branched alkyl C 1 to 12, which is optionally substituted by cyclohexyl or cyclopentyl; alkenyl C 2 to 6, which is optionally substituted by phenyl; or, when Z is —CO—ORa, hydrogen, and Rb and Rc, which are the same or different, are each alkyl C 1 to 12.

According to our invention we also provide a process for the production of a compound of formula I, which comprises reacting a compound of formula II,

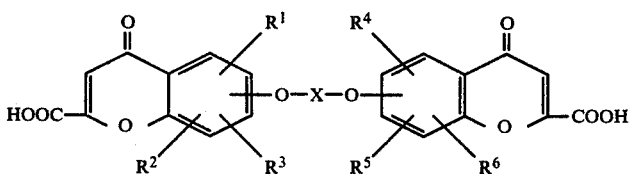

or a salt thereof,
in which R¹, R², R³, R⁴, R⁵, R⁶ and X are as defined above,
and a compound of formula III,

   III in which R and Z are as defined above, and
Y represents an anion forming group.

The anion forming group Y may be, for example, a halogen atom. When Y is halogen (preferably chlorine or bromine) the reaction is preferably carried out under anhydrous conditions, advantageously in the presence of an acid acceptor, e.g. an amine such as triethylamine or pyridine. The reaction is preferably carried out in the presence of a suitable solvent, e.g. dimethylformamide, tetrahydrofuran, piperidine or chloroform. The reaction may also be carried out in the presence of a catalytic amount of a quaternary ammonium compound, e.g. benzyltributylammonium chloride or benzyltriphenylphosphonium chloride. Desirably the reaction is carried out at a temperature of from about 0° C. to the boiling point of the solvent.

Compounds of formulae II and III are either known or may be made from known compounds using techniques known per se.

The compounds of formula I and the intermediates therefor may be isolated from their reaction mixtures using conventional techniques known per se.

The compounds of formula I are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen (see Example 27 of British Pat. No. 1,292,601). In man, both subjective and objective changes which result from the administration of specific antigen to sensitised subjects are inhibited by prior administration of the new compounds. Thus the new compounds are useful in the treatment of asthma, e.g. allergic asthma. The new compounds are also useful in the treatment of so-called 'intrinsic' asthma (in which no sensitivity to extrinsic antigen can be demonstrated). The new compounds are also of value in the treatment of other conditions in which antigen-antibody reactions are responsible for disease, for example, hay fever, certain eye conditions, e.g. conjunctivitis, alimentary allergy, e.g. urticaria and atopic eczema, and gastrointestinal allergy, especially in children, e.g. milk allergy.

The new compounds are also useful in the treatment of inflammatory and pruritic conditions.

For the above mentioned uses the dosage administered will of course, vary with the compound employed, the mode of administration and the treatment desired. However, in general, satisfactory results are obtained when the compounds are administered at a dosage of from 0.1 to 50 mg per kg of animal body weight in the test set out in Example 27 of British Pat. No. 1,292,601. For man the indicated total daily dosage is in the range of from 7 mg to 700 mg, and preferably from 14 mg to 210 mg, which may be administered in divided doses from 1 to 6 times a day or in sustained release form.

The compounds of formula I have the advantage that they are more efficacious in certain pharmacological models, or are more readily absorbed (as evidenced by plasma level), or are longer acting as measured by plasma half-life, or are more active or more readily absorbed when administered topically than compounds of formula I in which Q is hydrogen or an alkali metal atom.

$R^1$ to $R^6$ may be, for example, hydrogen, chlorine, bromine, hydroxy, ethyl, ethoxy, hydroxy-propoxy or ethoxy-ethoxy. It is preferred that all of $R^1$ to $R^6$ are hydrogen.

X may be a saturated or unsaturated hydrocarbon chain and is preferably substituted by a hydroxy group. Specific examples of the group X are groups of formulae:

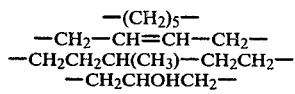

The group X is preferably a saturated hydrocarbon chain containing from 3 to 7 carbon atoms and is preferably substituted by a hydroxy group. A particularly preferred chain is of formula $-CH_2CHOHCH_2-$. It is also preferred that the chain should join the 5 and 5' positions on the chromone nuclei.

We prefer R to be hydrogen, alkyl C 1 to 4, phenyl or alkoxy (C 1 to 4)-carbonyl. We also prefer Z to be a group $-O-CO-Ra$. Ra is preferably hydrogen; straight or branched alkyl C 5 to 11 inclusive; or alkyl C 1 to 3 substituted by cyclohexyl or cyclopentyl; or alkenyl C 2 to 4 substituted by phenyl. Rb and Rc are preferably alkyl C 1 to 6, e.g. ethyl. Specific values of R which may be mentioned are methyl, phenyl and ethoxycarbonyl. Specific values of Ra which may be mentioned are styryl, trimethylmethyl, cyclohexyl, ethyl optionally substituted by cyclopentyl or cyclohexyl, or a group $-(CH_2)_nCH_3$ in which n is a whole number from 5 to 11 inclusive. The group Q is preferably pharmaceutically inert and should of course be non-toxic. We prefer those of the compounds of formula I having some or all of the following properties:

(a) A melting point of less than about 200° C., and preferably less than 130° C.

(b) A partition coefficient of between about 0.1 and 10, and preferably of about 2, between an aqueous buffer solution at pH 7.4 and n-octanol.

(c) An ability to be hydrolysed in human body fluids by a human esterase or lipase.

According to our invention we also provide a pharmaceutical composition comprising (preferably less than 80%, and more preferably less than 50% by weight) of a compound of formula I in combination with a pharmaceutically acceptable adjuvant, diluent or carrier. Examples of suitable adjuvants, diluents or carriers are:- for tablets, capsules and dragees; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; for inhalation compositions, coarse lactose; for topical compositions petrolatum, triacetin, isopropylmyristate or polyethylene glycol. For topical formulations we prefer the compound of formula I to comprise from 0.01 to 10% by weight of the composition. The compound of formula I when used as a solid is preferably in a form having a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be applied topically to the skin or to be administered oesophageally.

Some of the compounds of formula I are asymetric and may therefore exist in the form of two (or more) optical isomers or a racemic or other mixture of such isomers. The various optical isomers may be resolved, wholly or partially, using conventional techniques, e.g. chromatography, selective crystallisation etc. We prefer to use racemic or other mixtures of the compounds.

The invention is illustrated, but in no way limited by the following Examples, in which the temperatures are in °C.

EXAMPLE 1

Chloromethyl-3-cyclopentylpropionate

To a 100 ml round bottom flask was added 20.8 g 3-cyclopentylpropionic acid chloride (0.13 mole), 3.9 g paraformaldehyde (0.13 mole) and 100 mg anhydrous zinc chloride. The flask was protected from moisture with a drying tube and heated in an oil bath to 90° until a solution was obtained. The mixture was cooled, slurried in petroleum ether (30°–60°) and filtered. Solvent was removed from the filtrate in vacuo and the residue distilled (bp 68° @ 0.2 mm) to give 14.5 g (59%) of product: ir (neat), 1750 cm$^{-1}$; nmr (CDCl$_3$, TMS), δ 0.77–3.2 (m, 13H), 5.7 (s, 2H).

EXAMPLE 2

Chloromethyl dodecanoate

Lauroyl chloride (50.0 g, 0.23 mole), paraformaldehyde (6.9 g, 0.23 mole) and zinc chloride (100 g) were combined, protected with a drying tube and heated to 90° until a solution was obtained. The mixture was cooled, slurried with petroleum ether (30°–60°) and filtered. The filtrate was purified by passage through a 'Florisil' column ('Florisil' is a silica gel/magnesium silicate absorbent) and elution with petroleum ether (30°–60°). The column measured 45×5 cm and typically contained 350 g of Florisil. Removal of solvent gave 40 g (70%) of product: ir (neat), 1770 cm$^{-1}$; nmr (CDCl$_3$, TMS), δ 1.33 (m, 21H), 2.4 (M, 2H), 5.7 (s, 2H).

EXAMPLE 3 bis-Dodecanoyloxymethyl ester of 1,3-bis(2-carboxy-chromon-5-yloxy)propan-2-ol To a stirred solution of 3.5 ml triethylamine (0.022 mole) in 25 ml DMF was added portionwise 5.0 g 1,3-bis(2-carboxychromon-5-yloxy)propan-2-ol (0.011 mole). After a solution was obtained 5.5 g chloromethyl dodecanoate (0.022 mole) was added and the mixture was stirred under nitrogen overnight. The reaction mixture was diluted to 150 ml with ethylacetate and filtered. Washing with additional ethyl acetate made the solution cloudy so the filtrate was filtered through 'Celite' ('Celite' is a diatomaceous earth) the second time. The filtrate was transferred to a 500 ml separatory funnel and 250 ml H$_2$O was added. The mixture was allowed to stand unshaken for 15 min and the aqueous layer was separated. The organic layer was then washed with saturated NaHCO$_3$, allowed to stand unshaken for 15 min and the layers separated. The organic layer was dried (MgSO$_4$) and the solvent evaporated in vacuo to yield a white solid. This solid was slurried in a small amount of ethyl acetate and filtered to give 300 mg of product as a white solid with a slight greenish tint. After removal of solvent from the filtrate, the residue was slurried with ethanol and filtered to give 300 mg more of product. Analysis of residue remaining in the filtrate by nmr showed the presence of dimer $CH_3(CH_2)_{10}COOCH_2OOC(CH_2)_{10}CH_3$. The products were combined to give 600 mg (6%) of the title product: ir (KBr), 3400, 1750, 1650 cm$^{-1}$; nmr (CDCl$_3$, TMS), δ 0.63–3.63 (m, 46H), 4.47 (broad s, 5H), 6.03 (s, 4H), 6.77–7.90 (m, 8H).

Analysis—Theory: C, 65.90; H, 7.22; Found: C, 65.81; H, 7.34.

EXAMPLE 4 bis-N,N-Diethylcarbamoylmethyl ester of 1,3-bis(2-carboxychromon-5-yloxy)-propan-2-ol To a stirred solution of 3.5 ml triethylamine (0.022 mole) in 25 ml DMF was added portionwise 5.0 g 1,3-bis(2-carboxychromon-5-yloxy)-propan-2-ol (0.011 mole). After a solution was obtained, 3.3 g (0.022 mole) N,N-diethy chloroacetamide was added and the mixture was stirred under N$_2$ overnight. The DMF was removed on a rotary evaporator under high vacuum and the residue slurried with benzene several times and filtered. The filtered material was stirred in H$_2$O and filtered to give a solid. The filtrate from above was concentrated in vacuo, the residue stirred in ethyl acetate and filtered to give a white solid. The solids were combined to give 2.8 g of product. This was stirred with saturated NaHCO$_3$, filtered and washed with H$_2$O. After drying, 0.8 g of the title product (mp 160°–170° dec) remained: ir (BRr), 3380, 1740, 1640 cm$^{-1}$; nmr, (CDCl$_3$, TMS), 0.67–1.33 (m, 12H), 3.37 (m, 8H), 4.47 (broad singlet, 5H), 5.0 (s, 4H), 7.0 (m, 4H), 7.27 (d, 2H), 7.60 (t, 2H).

Analysis—Theory: C, 60.51; H, 5.51; N, 4.03; Found: C, 58.99; H, 5.52; N, 3.63.

EXAMPLE 5 bis-3-Cyclopentylpropionyloxymethyl ester of 1,3-bis(2-carboxychromon-5-yloxy)propan-2-ol To a solution of 3.5 ml triethylamine (0.022 mole) in 25 ml DMF was added portionwise 5.0 g 1,3-bis(2-carboxychromon-5-yloxy)propan-2-ol (0.011 mole). When a solution was obtained, 4.2 g 3-cyclopentylchloromethylpropionate (0.022 mole) was added and the mixture was stirred under nitrogen overnight. The reaction mixture was filtered and the DMF was removed on a rotary evaporator under high vacuum. The residue was slurried with ethyl acetate for 30–60 minutes with stirring. The ethyl acetate was decanted and the solvent removed in vacuo to give 6.6 g of crude product. Part of this residue was then purified by HPLC to give the pure title product, mp 102°–105°: ir (KBr), 3400, 1750, 1650 cm$^{-1}$; nmr, (CDCl$_3$, TMS).

EXAMPLE 6 bis-Pivaloyloxymethyl ester of 1,3-bis-(2-carboxychromon-5-yloxy)propan-2-ol

Disodium cromoglycate 5 g (9.8 mM) was dissolved in 80 ml H$_2$O. To this stirred solution was added 6.1 g (19.5 mM) benzyltributylammonium chloride and 80 ml CHCl$_3$. After 5 minutes stirring, 2.9 g (19.5 mM) chloromethylpivalate was added to the reaction mixture which was then stirred overnight. The CHCl$_3$ was then separated, dried (MgSO$_4$), and the solvent removed in vacuo. The residue was taken up in ethyl acetate and allowed to stand for several days. The resulting precipitate was filtered to give 2.3 g of the title compound. A second crop was obtained from the filtrate but this turned out to be benzyltributylammonium chloride. The solvent was removed from the filtrate and the the residue chromatographed on silica and eluted with 5% ethyl acetate/CHCl$_3$ to give an additional 1.7 g of the title compound mp 133°–135°; ir (KBr), 3440, 1740, 1645 cm$^{-1}$; nmr (CDCl$_3$, TMS), δ 1.27 (s, 18H), δ 4.48 (broad s, 5H), δ 6.0 (s, 4H), δ 6.75–7.31 (m, 6H), δ 7.63 (t, 2H).

Analysis—Theory: C, 60.34; H, 5.21; Found: C, 60.14; H, 5.16.

EXAMPLE 7 bis-Hexanoyloxymethyl ester of 1,3-bis-(2-carboxychromon-5-yloxy)propan-2-ol

To a solution of 5 g (9.8 mM) disodium cromoglycate in 100 ml H$_2$O was added 8.4 g (27 mM) benzyltributylammonium chloride and 50 ml CHCl$_3$. After 10 minutes stirring 3.2 g (19.5 mM) chloromethyl hexanoate was added and the reaction mixture was stirred overnight. The CHCl$_3$ layer was separated, dried (MgSO$_4$), and the solvent removed in vacuo. The residue was slurried in ethyl acetate and filtered to give 2.2 g of a white solid. One gram of this solid was chromatographed on silica and eluted with 3% ethyl acetate/CHCl$_3$ to give 300 mg of pure product and 400 mg of product with a trace of impurity. The filtrate yielded, after standing, 2.3 g of a precipitate which contained large amounts of benzyltributylammonium chloride. This residue was also chromatographed to give 400 mg of the title product and 400 mg of the title product with a trace of impurity. The two impure fractions were combined for rechromatography: mp 124°–126°; ir (KBr), 3400, 1740, 1645 cm$^{-1}$; nmr (CDCl$_3$, TMS) δ 0.64–2.67 (m, 22H), δ 4.47 (broad s, 5H), δ 6.0 (s, 4H), δ 6.87–7.34 (m, 6H), δ 7.6 (t, 2H).

Analysis—Theory: C, 61.32; H, 5.56; Found: C, 61.15; H, 5.58.

EXAMPLE 8

The following compounds may also be made by the method of the invention
Bis-3-(cyclohexanyl)propionyloxymethyl ester of 1,3-bis-(2-carboxychromon-5-yloxy)propan-2-ol
Bis-(cyclohexanyl)formyloxymethyl ester of 1,3-bis-(2-carboxychromon-5-yloxy)propan-2-ol
Bis-octanoyloxymethyl ester of 1,3-bis-(2-carboxychromon-5-yloxy)propan-2-ol.

EXAMPLE 9 bis-Diethyl malonyl ester of 1,3-bis-(2-carboxychromon-5-yloxy)propan-2-ol

To 25 ml of water was added 1 g (1.95 mmole) of disodium cromoglycate and 1.2 g (4 mmole) of benzyltributyl ammonium chloride. The solution was stirred for 10 minutes and 25 ml of chloroform was added. The mixture was stirred rapidly for 3 hours and the chloroform layer was separated and dried (MgSO$_4$). The chloroform was filtered and the solvent removed. The residue was dissolved in 20 ml dimethylformamide and 540 mg (2.8 mmole) diethyl chloromalonate was added. The solution was stirred under nitrogen for 2 days and the solvent was evaporated. The residue was slurried in diethyl ether and the ether was decanted and discarded. The residue was dissolved in ethyl acetate and the ethyl acetate was washed with water, dried (MgSO$_4$), and evaporated. The residue was chromatographed on silica gel and eluted with 3% ethyl acetate/chloroform to give the title product: mp 140°-142°; ir (KBr), 3400, 1740, 1640 cm$^{-1}$; nmr (CDCl$_3$, TMS), 1.33 (t, 12H), 4.10–4.77 (m, 13H), 5.7 (s, 2H), 6.8–7.33 (m, 6H), 7.63 δ (t, 2H).

Analysis calculated for C$_{37}$H$_{36}$O$_{19}$: C, 56.63; H, 4.62; Found: C, 55.88; H, 4.77.

EXAMPLE 10 bis-Cinnamoyloxybenzyl ester of 1,3-bis-(2-carboxychromon-5-yloxy)propan-2-ol 1.8 g (3.5 mmole) of disodium cromoglycate and 2.2 g (7 mmole) benzyltributylammonium chloride were dissolved in 25 ml of water, 25 ml of chloroform were added and the mixture stirred for 1 hour. Chlorobenzylcinnamoate (1.9 g, 7 mmole) was added and the mixture was stirred for four hours. The chloroform layer was separated, dried (MgSO$_4$), filtered and the solvent removed. The residue was chromatographed on silica gel and eluted with chloroform to give the desired product which was characterised by standard methods.

Chlorobenzylcinnamoate

Benzaldehyde (20.1, 0.19 mole) was rapidly stirred while 31.7 (0.19 mole) of cinnamoyl chloride was added portionwise (exothermic reaction). After addition, the mixture was allowed to stand 2 hours under nitrogen and the resulting solid was recrystallised from 30°–60° petroleum ether to give the sub-title product.

EXAMPLE 11

1,3-Bis-[2-(1-hexanoyloxyethyl-1-carboxy)chromon-5-yloxy]propan-2-ol

Disodium cromoglycate (5 g, 9.8 mmole) and 6.1 g benzyltributylammonium chloride (19.5 mmole) were dissolved in 80 ml of water. To this solution was added 100 ml of chloroform and the mixture was rapidly stirred for 2 hours. The chloroform layer was separated, dried (MgSO$_4$), and added to a 250 ml flask. α-Chloroethyl hexanoate (3.5 g, 19.5 mmole) was added to the solution and the reaction mixture was stirred under nitrogen for 7 days. The chloroform was evaporated and the residue was partitioned between ether and water. The water layer was extracted with a second portion of ether and the organic layers were combined, dried (MgSO$_4$) and evaporated. The residue was then slurried twice with ligroin and the ligroin was decanted and discarded. The remaining residue was purified by column chromatography on silica and eluting with chloroform to give the title compound as a yellow glass: ir (CHCl$_3$); 3390, 1750, 1650 cm$^{-1}$; nmr (CDCl$_3$, TMS), 0.63–1.97 (m, 24H), 2.10–2.57 (m, 4H), 4.20–4.73 (broad s, 5H), 6.83–7.27 (m, 8H), 7.62 (t, 2H).

Analysis calculated for C$_{39}$H$_{44}$O$_{15}$: C, 62.22; H, 5.89; Found: C, 62.08; H, 5.95.

EXAMPLE 12

Bis-t-Butyl acetate ester of 1,3-bis-(2-carboxychromon-5-yloxy)propan-2-ol

Disodium cromoglycate (5 g, 9.8 mmol) was stirred in 20 ml water for 15 min followed by addition of 6.1 g (19 mmol) of benzyltributylammonium chloride. The solution was stirred for 1 hr and 25 ml chloroform was added. This two-phase system was stirred for 4 hr and the chloroform layer was separated, dried (MgSO$_4$) and the solvent evaporated in vacuo. t-Butyl chloroacetate (10 ml) was added to the residue and the mixture was stirred under nitrogen overnight. The mixture was diluted with 150 ml ethyl acetate and this solution was washed twice with water, dried (MgSO$_4$), and the solvent removed in vacuo. The resulting solid was slurried in petroleum ether (30°–60°) and filtered to give 2.3 g of product which was suitably pure for further reaction. Analytically pure material was obtained by chromatography on silica gel and elution with chloroform, mp 149°–150°, ir (KBr) 3385, 1730, 1650, 1600 cm$^{-1}$; nmr (CDCl$_3$, TMS) δ 1.50 (s, 18H), 4.43–4.77 (m, 9H) 7.03 (m, 6H), 7.61 (t, 2H).

Analysis Calculated for C$_{35}$H$_{36}$O$_{15}$: C, 60.34; H, 5.21; Found: C, 60.48; H, 5.29.

EXAMPLE 13

Bis-Glycolic acid ester of 1,3-bis-(2-carboxychromon-5-yloxy)propan-2-ol

To a solution of 10 ml dichloromethane saturated with hydrogen chloride at −10° was added 600 mg of the bis-t-butyl acetate ester product of Example 12. The mixture was stoppered and stored at −20° for 24 hours. The dichloromethane was decanted and discarded. The remaining solid was slurried in chloroform and filtered to give 268 mg of the title product mp 278° dec: ir (KBr), 3380, 1725, 1630, 1590 cm$^{-1}$; mnr (d$_6$—DMSO, TMS), δ 4.37 (broad s, 5H), 4.73–5.13 (m, 4H), 6.80 (s, 2H), 7.0–7.5 (m, 4H), 7.77 (t, 2H).

Analysis Calculated for C$_{27}$H$_{20}$O$_{15}$: C, 55.48; H, 3.45; Found: C, 54.70; H, 3.35.

We claim:

1. A compound of formula I,

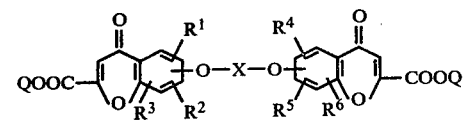

in which
R$^1$, R$^2$, R$^3$, R$^4$, R$^5$ and R$^6$ are the same or different and each represent hydrogen, halogen, hydroxy, alkyl C 1 to 6, alkoxy C 1 to 6, hydroxy-alkoxy C 1 to 6, or alkoxy C 1 to 6-alkoxy C 1 to 6, X is a straight or branched C 2 to 10 hydrocarbon chain which may be substituted by an —OH group, Q is a group —CHR—Z, R is hydrogen, alkyl C 1 to 8, or phenyl, Z is a group —O—CO—Ra, —CO—ORa or —CONRbRc, Ra is cyclohexyl or cyclopentyl; straight or branched alkyl C 1 to 12, unsubstituted or substituted by cyclohexyl or cyclopentyl; alkenyl C 2 to 6, unsubstituted or substituted by phenyl; or, when Z is —CO—ORa, hydrogen, and Rb and Rc, which are the same or different, are each alkyl C 1 to 12.

2. A compound according to claim 1, wherein all of R$^1$ to R$^6$ are hydrogen.

3. A compound according to claim 1, wherein X is a saturated hydrocarbon chain containing from 3 to 7 carbon atoms and is substituted by an —OH group.

4. A compound according to claim 3, wherein the group X is of formula —CH$_2$CHOHCH$_2$—.

5. A compound according to claim 4, wherein the —OXO— chain joins the 5,5' positions on the chromone nuclei.

6. A compound according to claim 1, wherein Z is a group —O—CO—Ra.

7. A compound according to claim 1, wherein Ra is hydrogen; straight or branched alkyl C 5 to 11 inclusive; or alkyl C 1 to 3 substituted by cyclohexyl or cyclopentyl; or alkenyl C 2 to 4 substituted by phenyl.

8. A compound according to claim 7, wherein Ra is styryl, trimethylmethyl, cyclohexyl, ethyl unsubstituted or substituted by cyclopentyl or cyclohexyl, or a group —(CH$_2$)$_n$CH$_3$ in which n is a whole number from 5 to 11 inclusive.

9. A compound according to claim 1 and having a melting point of less than 200° C.

10. A compound according to claim 1 and having a partition coefficient of from 0.1 to 10 between an aqueous buffer solution at pH 7.4, and n-octanol.

11. A compound selected from
bis-Dodecanoyloxymethyl ester of 1,3-bis(2-carboxychromon-5-yloxy)propan-2-ol,
bis-N,N-Diethylcarbamoylmethyl ester of 1,3-bis(2-carboxychromon-5-yloxy)-propan-2-ol,
bis-3-Cyclopentylpropionyloxymethyl ester of 1,3-bis(2-carboxychromon-5-yloxy)propan-2-ol,
bis-Pivaloyloxymethyl ester of 1,3-bis-(2-carboxychromon-5-yloxy)propan-2-ol,
bis-Hexanoyloxymethyl ester of 1,3-bis-(2-carboxychromon-5-yloxy)propan-2-ol,
bis-3-(Cyclohexanyl)propionyloxymethyl ester of 1,3-bis-(2-carboxychromon-5-yloxy)propan-2-ol,
bis-(Cyclohexanyl)formyloxymethyl ester of 1,3-bis-(2-carboxychromon-5-yloxy)propan-2-ol,
bis-Octanoyloxymethyl ester of 1,3-bis-(2-carboxychromon-5-yloxy)propan-2-ol,
bis-Diethyl malonyl ester of 1,3-bis-(2-carboxychromon-5-yloxy)propan-2-ol,
bis-Cinnamoyloxybenzyl ester of 1,3-bis-(2-carboxychromon-5-yloxy)propan-2-ol,
1,3-Bis-[2-(1-hexanoyloxyethyl-1-carboxy)chromon-5-yloxy]propan-2-ol,
bis-t-Butyl acetate ester of 1,3-bis-(2-carboxychromon-5-yloxy)propan-2-ol, and
bis-Glycolic acid ester of 1,3-bis-(2-carboxychromon-5-yloxy)propan-2-ol.

* * * * *